US012471973B2

(12) United States Patent
Touchet et al.

(10) Patent No.: US 12,471,973 B2
(45) Date of Patent: Nov. 18, 2025

(54) THREADED IMPLANT FOR BONE FIXATION AND RELATED METHODS

(71) Applicant: Trilliant Surgical LLC, Houston, TX (US)

(72) Inventors: Tyler Joseph Touchet, Cypress, TX (US); Mia Fiacchi, Houston, TX (US)

(73) Assignee: Trilliant Surgical LLC, Houston, TX (US)

( * ) Notice: Subject to any disclaimer, the term of this patent is extended or adjusted under 35 U.S.C. 154(b) by 365 days.

(21) Appl. No.: 18/082,172

(22) Filed: Dec. 15, 2022

(65) Prior Publication Data

US 2023/0190348 A1 Jun. 22, 2023

Related U.S. Application Data

(60) Provisional application No. 63/290,851, filed on Dec. 17, 2021.

(51) Int. Cl.
*A61B 17/86* (2006.01)

(52) U.S. Cl.
CPC ........ *A61B 17/863* (2013.01); *A61B 17/8635* (2013.01)

(58) Field of Classification Search
CPC .......................... A61B 17/863; A61B 17/7225
See application file for complete search history.

(56) References Cited

U.S. PATENT DOCUMENTS

2017/0086885 A1* 3/2017 Duncan .............. A61B 17/7041
2021/0369314 A1* 12/2021 Preiss-Bloom ....... A61L 31/128

* cited by examiner

*Primary Examiner* — Olivia C Chang
(74) *Attorney, Agent, or Firm* — Veros Legal Solutions, LLP

(57) ABSTRACT

A threaded implant for bone fixation is provided. The implant includes a head. The implant includes a shaft extending distally from the head. The shaft includes a distal tip. The shaft includes a first set of threads extending a first predetermined length from the distal tip. The first set of threads are configured to capture cortical bone in one of a foot and/or ankle bone of a patient. The shaft includes a second set of threads extending a second predetermined length from the first set of threads. The second set of threads configured to capture epiphyseal bone in the one of the foot and/or ankle bone. Related methods are also provided.

25 Claims, 6 Drawing Sheets

THREADED IMPLANT FOR BONE FIXATION AND RELATED METHODS

CROSS-REFERENCE TO RELATED APPLICATIONS

This application is related to, and claims priority to U.S. Provisional Patent Application Ser. No. 63/290,851, filed on Dec. 17, 2021, and entitled THREADED IMPLANT FOR BONE FIXATION AND RELATED METHODS, the contents of which is hereby incorporated by reference in its entirety.

FIELD

The present disclosure relates to threaded implants for bone fixation, systems including the same, and related methods.

BACKGROUND

Medial malleolar fractures are one of the most common fracture types in the ankle joint. Standard AO fixation practices for medial malleolar fractures include the use of two partially threaded cancellous screws. However, non-union rate and screw backout rate are common at least in part because current implants do not account for the varying bone density of the tibia. More specifically, the epiphyseal scar of the distal tibia has the relatively densest bone, and the distal metaphysis has a comparatively decreased bone density, especially in elderly patients who have higher incidence of osteoporotic bone. Research has shown that screws engaging the epiphyseal scar have more compression force on the fracture line than screws engaging the medullary region. The different bone densities require different fixation methods and the current fixation technique for medial malleolus fractures, which utilize two partially threaded cancellous screws, only takes one such bone density into account. There are no devices on the market that can capture all bone densities in the distal tibia to provide maximum fixation for medial malleolus fractures.

Malleolar fracture fixation utilizing partially threaded cancellous screws has a major disadvantage of lack of secure bone purchase within the distal tibial metaphysis, specifically the epiphyseal scar and distal cortices of the tibia, which have varying bone densities. In order to obtain secure bone purchase of the distal metaphysis, fixation screws must be long. However, fixation screws of excessive length do not provide secure bone purchase of the cancellous bone of the metaphysis.

Accordingly, a need exists for new, specialized threaded implants for bone fixation, systems including the same, and/or related methods, which provide fixation to fractures of the foot and/or ankle.

SUMMARY

In some embodiments, a threaded implant for bone fixation is provided. The implant includes a head. The implant includes a shaft extending distally from the head. The shaft includes a distal tip. The shaft includes a first set of threads extending a first predetermined length from the distal tip. The first set of threads are configured to capture cortical bone in one of a foot and/or ankle bone of a patient. The shaft includes a second set of threads extending a second predetermined length from the first set of threads. The second set of threads configured to capture epiphyseal bone in the one of the foot and/or ankle bone.

In some embodiments, a method of utilizing a threaded implant for bone fixation is provided. The method includes disposing a distal tip of a shaft of the threaded implant adjacent to or against a surface of a foot and/or ankle bone of a patient. The method includes rotationally driving a head of the threaded implant that is coupled to the shaft until a first set of threads, extending a first predetermined length from the distal tip, capture cortical bone in the foot and/or ankle bone, and a second set of threads, extending a second predetermined length from the first set of threads, capture epiphyseal bone in the foot and/or ankle bone.

In some embodiments, a method of manufacturing a threaded implant for bone fixation is provided. The method includes forming a head of the threaded implant. The method includes forming a shaft extending distally from the head. The shaft includes a distal tip. The shaft includes a first set of threads extending a first predetermined length from the distal tip. The first set of threads are configured to capture cortical bone in one of a foot and/or ankle bone of a patient. The shaft includes a second set of threads extending a second predetermined length from the first set of threads. The second set of threads are configured to capture epiphyseal bone in the one of the foot and/or ankle bone.

BRIEF DESCRIPTION OF THE DRAWINGS

A more complete appreciation of the subject matter of the present disclosure and of the various advantages thereof can be realized by reference to the following detailed description in which reference is made to the accompanying drawings in which.

DETAILED DESCRIPTION

Figure 1:
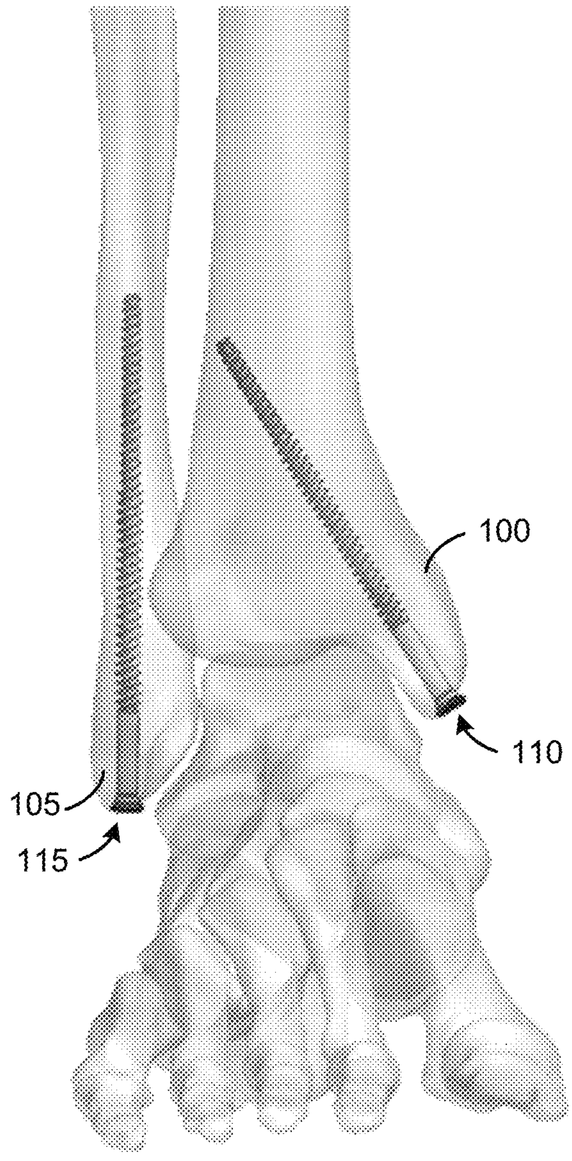
FIG. 1 illustrates a frontal view of the skeletal structure of a lower leg of a patient stabilized using threaded implants for bone fixation, in accordance with some example embodiments.

Implementations of the technology described herein are directed generally to threaded implants for bone fixation, systems including the same, and related methods. The following description and examples illustrate some exemplary implementations, embodiments, and arrangements of the disclosed invention in detail. Those of skill in the art will recognize that there are numerous variations and modifications of this invention that are encompassed by its scope. Accordingly, the description of a certain example embodiment should not be deemed to limit the scope of the present invention.

Example Embodiments

Implants described herein have advantages over current offerings due at least in part to novel, non-obvious and inventive variations in thread geometries configured to capture bone having different densities for fracture fixation. For example, implants disclosed herein comprise specialized threads and advantageously ensure maximum bone purchase within the epiphyseal scar and distal cortices of a foot and/or ankle bone, such as but not limited to the distal tibia. In some embodiments, such specialized threads have varying diameters configured for optimal function and bone purchase within the respective cancellous and cortical portions of the bone, varying lengths of cancellous threads, varying lengths of cortical threads for use in, for example and not limitation, the medial and lateral malleolus, and varying pitches of such threads to maximize and/or optimize implant surface area.

While several embodiments having specific features are disclosed herein, any one or more embodiments expressly or inherently described, or implied herein may have different types of threads (e.g., buttress, V-threads, square threads, etc); different numbers of leads (e.g., single, double, triple, etc.); different head options (e.g., headed or headless while still retaining features sufficient to be driven into bone); may be fully or partially threaded, and/or cannulated or non-canulated.

An important feature of implants as described herein is a need to prevent pull through or pull out of the implant from the bone after implantation. Accordingly, any embodiment described herein may be cannulated to increase fixation strength, for example within osteoporotic bone, as cannulation has been shown to help decrease the rate of nonunion and screw backout, for example and not limitation, in malleolar fractures. In addition, cannulation may allow such implants to accept a standard 0.62 K-wire.

Implants as described herein may be compatible with bone plates, including but not limited to tension band plates, as the usage of bone can provide fixation for foot and/or ankle fractures, including but not limited to transverse and avulsion type fractures. Such implants have been manufactured and implanted into cadavers by surgeons.

Many features of the implants disclosed herein compliment the anatomy for which the implants will be used, and the goals for fixation. For example, the epiphyseal scar includes dense bone, that when used for fracture fixation, may provide a relatively high amount of compression compared to other bone fixation locations. Additional features of such implants are described below.

As evidence of the novelty, non-obviousness and inventiveness of embodiments described anywhere herein, no other implant on the market incorporates the variation of features and threads to provide bone purchase in differing bone densities, as described herein, despite the above-described need in the industry. Several aspects of embodiments as described anywhere herein will now be described in connection with one or more of the following figures.

Figure 3:
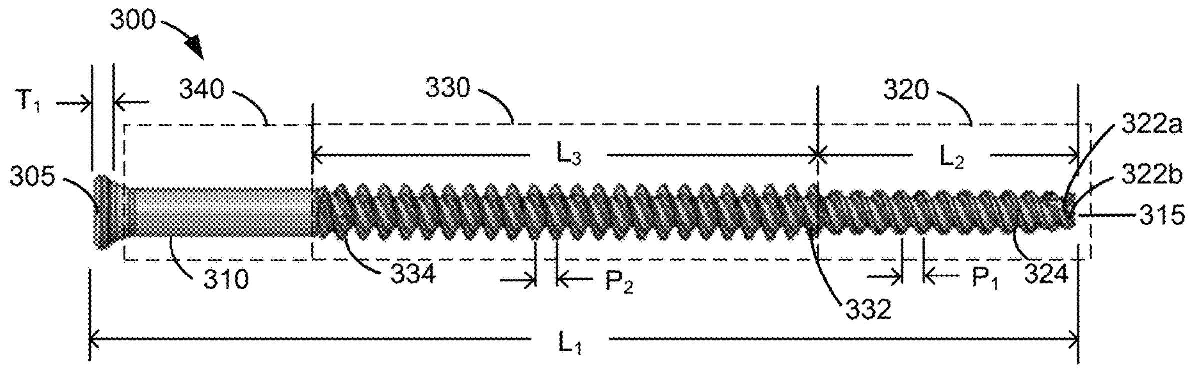
FIG. 3 illustrates a threaded implant for bone fixation, in accordance with some example embodiments.
Figure 4:
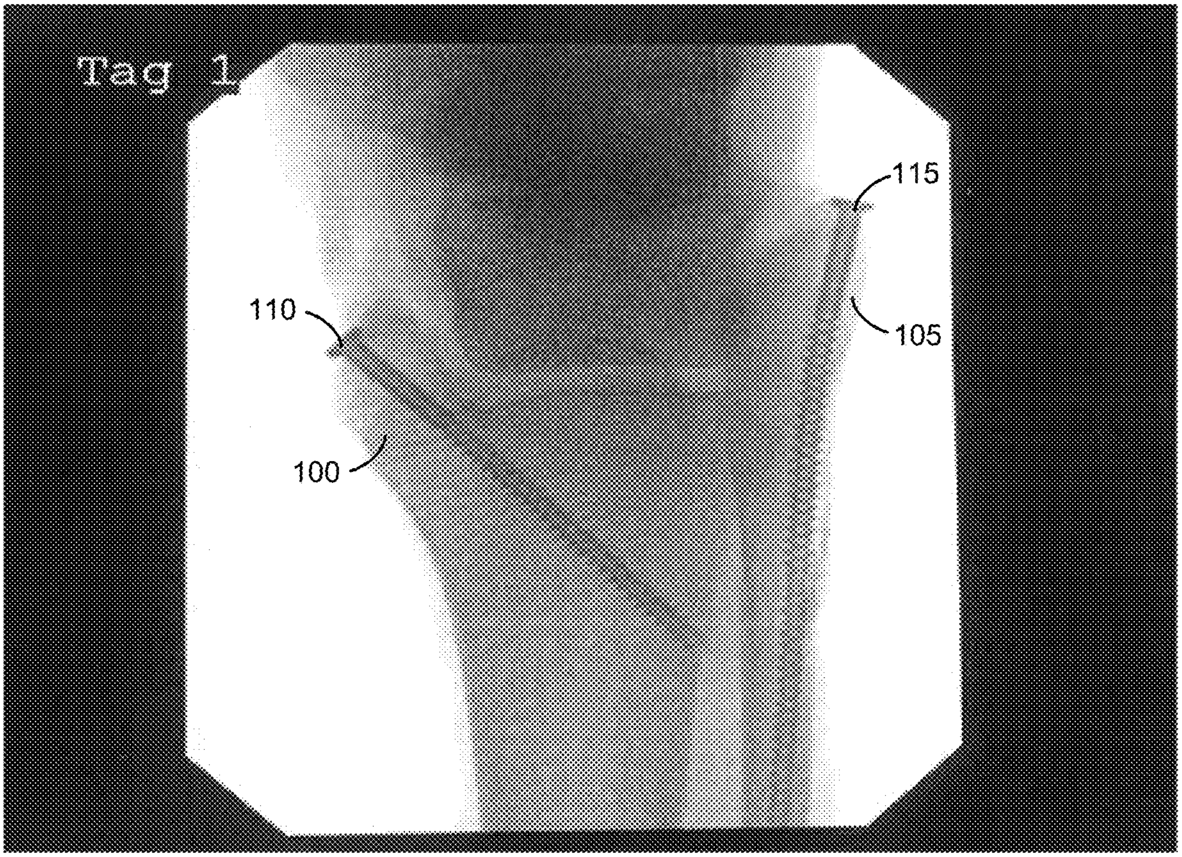
FIG. 4 is an x-ray of a skeletal structure of a lower leg of a patient stabilized using threaded implants for bone fixation, similar to that shown in FIG. 1, in accordance with some example embodiments.

FIG. 1 illustrates a frontal view of a skeletal structure of a lower leg of a patient stabilized using threaded implants 110, 115 for bone fixation, in accordance with some example embodiments. First and second implant(s) 110, 115 are illustrated as being implanted into a right tibia 100 and fibula 105 of a $50^{th}$ percentile male, respectively. FIG. 4 illustrates an x-ray image of a skeletal structure of a lower leg of a patient stabilized using threaded implants 110, 115, similar to that illustrated in FIG. 1 and/or as described anywhere in this disclosure. Example embodiments of either or both of threaded implants 110, 115 are described in more detail in connection with at least FIG. 3. Accordingly, threaded implants 110, 115 may each be embodiments of implant 300. Implant 300 is specifically designed for fixation and stabilization of a foot and/or ankle bone, such as but not limited to the medial malleolus, with added capabilities of acting as an intermedullary (IM) nail. In some embodiments, insertion of two implants 110 as well as bicortical fixation can ensure the torsional forces on the bone, e.g., the medial malleolus, are stabilized.

Implant 300 comprises a head 305 and a shaft 310. Shaft 310 is coupled to head 305 and extends distally of head 305. A consideration related to procedures in which implant 300 may be used, for example and not limitation, is the prominent ends of the medial and lateral malleoli. To decrease irritation and palpability to these areas, head 305 of implant 300 may be smoothed and have a thickness $T_1$ of about 1.60 mm. In some embodiments, head 305 may have a diameter of 6.0 mm, which enables head 305 to sit within bone plate holes, including but not limited to the locking and non-locking Arsenal holes. In some embodiments, a drive feature such as a hexalobe drive feature, cruciform drive feature, or other suitable drive feature, is also disposed within head 305 so implant 300 may be compatible with existing instruments. In some embodiments, implant 300 may be dual lead to decrease insertion time.

Head 305 and shaft 310 may have a total implant length $L_1$. The total length of implant 300 may vary depending on the intended application. For example, implant length $L_1$ may vary from 65 mm to 120 mm, in 5 mm increments. Different lengths allow for fixation in different sized patients, at different sites, for different fracture sizes, and utilizing implant 300 in different capacities (e.g., as an intermedullary nail (IM), or as a lag screw). For example, and not limitation, longer lengths would be used to mimic an intermedullary canal for fractures in the lateral malleolus of fibula 105, whereas shorter lengths would be used for the medial malleolus fractures of tibia 110. In some embodiments, implant 300 may comprise Titanium-6Aluminum-4Vanadium per ASTM F-136.

A distal tip 315 of shaft 310 and/or implant 300 is tapered to decrease insertion torque. In some embodiments, distal tip 315 has a 6.35 mm taper of 2.25 degrees, which may be chosen due to its non-compromising wall thickness of implant 300. Such a taper also provides for easy entry of implant 300 into the bone. A proximal portion 340 of implant 300 is not threaded as this part will not pass the fracture line. Non-threaded proximal portion 340 also mimics the AO technique of using partially treaded screws for malleolar fixation utilizing a lag technique.

Between distal tip 315 and proximal portion 304, shaft 310 comprises a first set/type 320 of threads 324 and a second set/type 330 of threads 334. In some embodiments first set 320 of threads 324 may also be referred to as distal threads or cortical threads, and vice versa. Likewise, in some embodiments second set 330 of threads 334 may also be referred to as proximal threads or cancellous threads, and vice versa. In some embodiments, a diameter of the shaft 310 along first 320 and second 330 sets of threads may be about 2.3 mm, which is between a recommended diameter for a cancellous screw (e.g., 3.0 mm) and a recommended diameter for a cortical screw (e.g., 2.0 mm).

In some embodiments, first set 320 of threads 324 are configured to provide fixation of the distal cortices of tibia 100 and to increase fixation strength (e.g., by about six times) by maximizing thread count beyond the fracture line. First set 320 of threads 324 extends for a thread length $L_2$, from a distal end of second set 330 of threads 334 to distal tip 315 of shaft 310 and/or implant 300. In some embodiments, $L_2$ varies with the total length $L_1$ of implant 300. In some embodiments, a diameter of threads 324 is 3.5 mm, as recommended for bicortical fixation since this diameter has proven to provide resistance to translational forces and increased pull out strength. Threads 324 also taper at a distal portion of first set 320 as they approach distal tip 315. In this way decreased insertion torque may be achieved. A pitch $P_1$ of threads 324 is minimized to ensure implant 300 has maximum surface area of maximum thread purchase into the bone. In some embodiments, $P_1$ is 3.5 mm.

In some embodiments, second set 330 of threads 334 are disposed closer to head 305 of implant 300 than first set 320 and are configured to capture the dense bone in the epiphyseal scar in tibia 100, as this has proved to provide more compression force than if implant 300 were to enter through the medullary region of tibia 100.

In some embodiments, $L_3$ has a constant value of 40 mm, regardless of implant length $L_1$, as research has shown 40 mm to be the optimal screw length for epiphyseal scar (dense bone) capture. However, the present disclosure is not so limited and any other suitable length $L_2$ is also contemplated. In some embodiments, a diameter of threads 334 is 4.5 mm, as recommended for medial malleolar screws by the AO-ASIF Group. Such a diameter of threads 334, being between 4.5 mm and 5.0 mm, allows implant 300 to act as a fibular IM nail, in some embodiments and if desired, in addition or alternative to being utilized to have a tibial lag bolt function. Fibular IM nail and tibial lag bolt functionalities are both discussed in more detail below. A pitch $P_2$ of threads 334 is also minimized to ensure implant 300 has maximum surface area of maximum thread purchase into the bone. In some embodiments, $P_2$ is the same as $P_1$, e.g., 3.5 mm, thereby aiding insertion of implant 300 beyond the proximal edge of first set 320 of threads 324.

Accordingly, in some embodiments, a diameter of the shaft coextensive with first 320 and second 330 sets of threads 324, 334 is approximately 50% of a diameter of second set 330 of threads 334. In some embodiments, a diameter of first set 320 of threads 324 is approximately 75% of the diameter of second set 330 of threads 334.

An additional feature of implant 300 are a plurality of cutting flutes **322*a*, 322*b* and 332, which give implant 300 self-tapping abilities to ensure low insertion torque and for machinability. A first 322*a* and second 322*b* cutting flute are each disposed immediately adjacent distal tip 315 of implant 300 to aid initial insertion. In some embodiments, first and second cutting flutes 322*a*, 322*b* are disposed at diametrically opposite positions at or immediately adjacent distal tip 315. A third cutting flute 334 is disposed at or immediately adjacent a transition from first set 320 of threads 324 to second set 330 of threads 334 to aid insertion of threads 334**.

In some embodiments, implant 300 is specifically configured to fixate fractures of the medial malleolus and of the lateral malleolus. The specific medial malleolus fracture patterns implant 300 can fixate include but are not limited to vertical, oblique and transverse. Implant 300 is also configured to treat all three of the Weber fractures. Discussion of tibial lag screw/bolt and fibular IM nail functionalities now follows.

Lag Screw Function of Implant 300

Figure 2A:
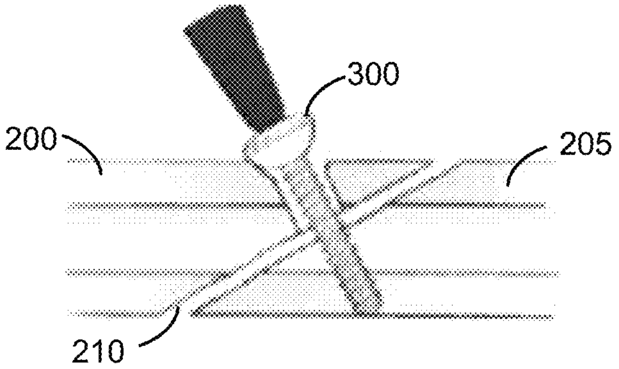
FIG. 2A illustrates a bone screw being driven into two portions of bone adjacent to a fracture in a direction perpendicular to a plane of the fracture, in accordance with some example embodiments.
Figure 2B:
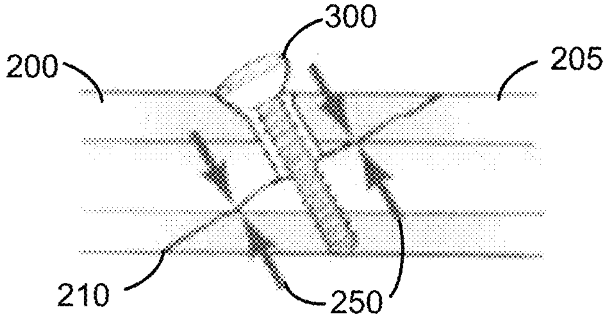
FIG. 2B illustrates the arrangement of FIG. 2A with the bone screw driven sufficiently to pull the two portions of bone together, in accordance with some example embodiments.
Figure 2C:
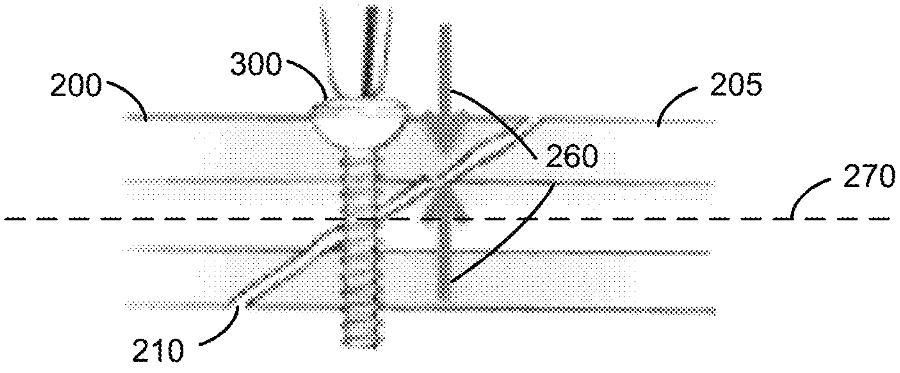
FIG. 2C illustrates a bone screw being driven into two portions of bone adjacent to a fracture in a direction perpendicular to a long axis of the bone, in accordance with some example embodiments.

One function of implant 300 is to act as a lag screw. For example, depending on how lag screw 300 is inserted, it can provide inter-fragmentary compression (see FIGS. 2A and 2B), or resistance to shear forces from axial loading (see FIG. 2C). Briefly, FIG. 2A illustrates two adjacent fragments of bone 200, 205 separated by a fracture line 210. To provide maximum interfragmentary compression 250, a gliding hole may be predrilled perpendicular to fracture line 210 through the first cortex 200 only, followed by the insertion of implant 300 (e.g., medial malleolus implant). FIG. 2B illustrates implant 300 so disposed and installed. To provide resistance 260 to shear forces from axial loading of tibia 100, implant 300 may be inserted perpendicular to the long axis 270 of the bone 200, 205. Implant 110 in FIG. 1 illustrates a use as a lag screw. Osteoporotic bone has an increased probability of implant pull through. Since implant 300 has considerable use with osteoporotic bone, and to further decrease the probability of implant pull through, a washer (not shown) may be used in conjunction with implant 300. Implant 300 may also be used as a lag screw in conjunction with a plate.

Intermedullary Nail Function of Implant 300

Another function of implant 300 is to act as an IM nail for fibula fractures. A purpose of an IM nail is to re-establish length, alignment, and rotation of the limb, which are commonly compromised from Weber fractures. In some embodiments, implant 300 can be inserted through the distal portion of fibula 105 and act as a load sharing device. Using implant 300 as an IM nail can also reduce wound complications, as the procedure is usually minimally invasive. Implant 105 in FIG. 1 illustrates a use as an IM nail.

Example Method(s) of Use

Figure 5:
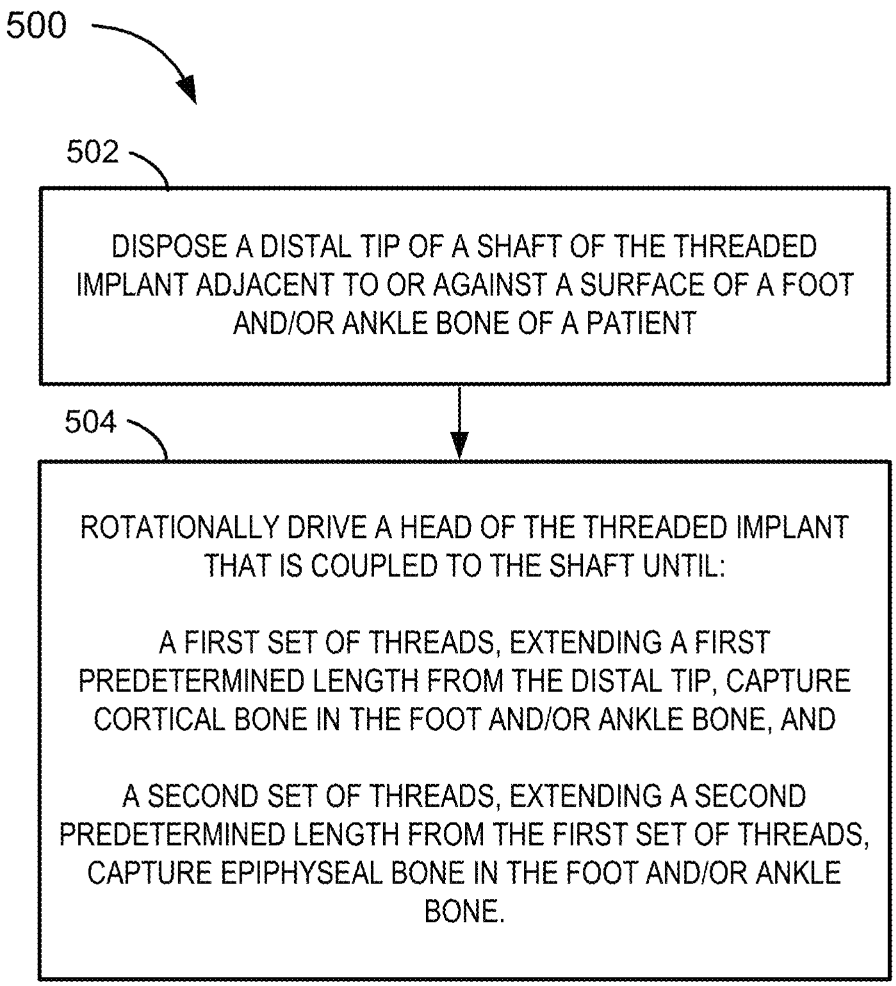
FIG. 5 illustrates a flowchart related to a method of using a threaded implant for bone fixation, in accordance with some example embodiments.

The disclosure now turns to FIG. 5 and one or more example methods of using a threaded implant for bone fixation, as described anywhere in this disclosure. Although particular steps are described herein, the present application is not so limited and alternative methods may include a subset of these steps, in the same or different order, and may additionally include one or more addition steps not described herein.

Step 502 includes disposing a distal tip of a shaft of the threaded implant adjacent to or against a surface of a foot and/or ankle bone of a patient. For example, as previously described in connection with at least FIGS. 1-4, distal tip 315 of shaft 310 of implant 300 may be disposed adjacent to or against a surface of tibia 100 or of fibula 105 of a patient (see, e.g., FIGS. 1-2C).

Step 504 includes rotationally driving a head of the threaded implant that is coupled to the shaft until a first set of threads, extending a first predetermined length from the distal tip, capture cortical bone in the foot and/or ankle bone, and a second set of threads, extending a second predetermined length from the first set of threads, capture epiphyseal bone in the foot and/or ankle bone. For example, as previously described in connection with at least FIGS. 1-4, head 305 of implant 300, which is coupled to shaft 310, may be driven into tibia 100 or fibula 105 until first set 320 of threads 324 capture cortical bone in tibia 100 or fibula 105, and second set 330 of threads 334 capture epiphyseal bone in tibia 100 or fibula 105.

In some embodiments, a method related to flowchart 500 may optionally include pre-drilling a gliding hole perpendicular to a fracture line and through a first cortex only, followed by insertion of implant 300 (see, e.g., fracture line 210 and first cortex 200 in FIGS. 2A-2B).

Example Methods of Manufacture

Figure 6:
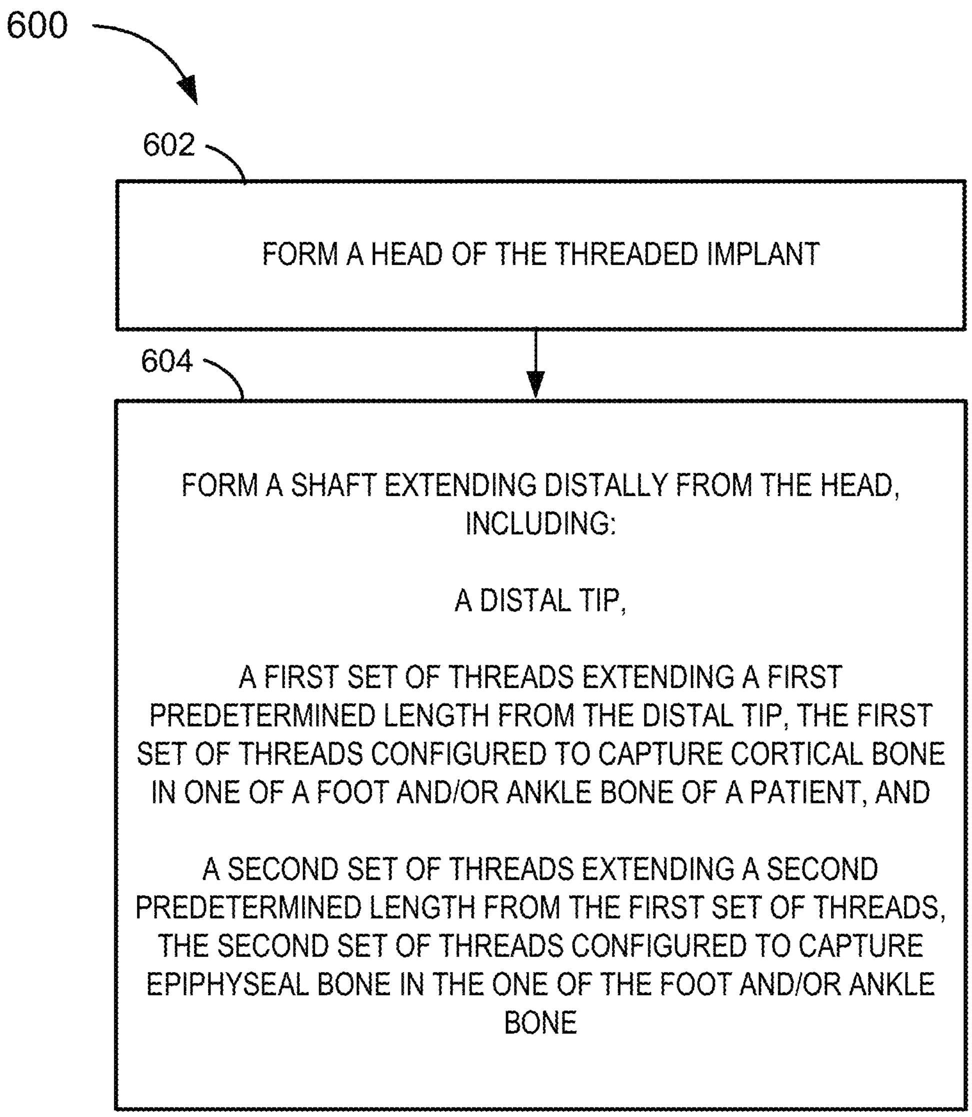
FIG. 6 illustrates a flowchart related to a method of manufacturing a threaded implant for bone fixation, in accordance with some example embodiments.

The disclosure now turns to FIG. 6 and one or more example methods of manufacturing a threaded implant for bone fixation, as described anywhere in this disclosure. Although particular steps are described herein, the present application is not so limited and alternative methods may include a subset of these steps, in the same or different order, and may additionally include one or more addition steps not described herein.

Step 602 includes forming a head of the threaded implant. For example, as previously described in connection with at least FIGS. 1-4, Implant 300 may be manufactured by forming head 305.

Step 604 includes forming a shaft extending distally from the head and comprising a first set of threads extending a first predetermined length from the distal tip, the first set of threads configured to capture cortical bone in one of a foot and/or ankle bone of a patient, and a second set of threads extending a second predetermined length from the first set of threads, the second set of threads capture epiphyseal bone in the one of the foot and/or ankle bone. For example, as previously described in connection with at least FIGS. 1-4, shaft 310 may be formed to extend distally from head 305. Shaft 310 may be formed to include first set 320 of threads 324 extending first predetermined length $L_2$ from distal tip 315. First set 320 of threads 324 are configured to capture cortical bone in tibia 100 and/or fibula 105 of a patient. Shaft 310 may be further formed such that second set 330 of threads 334 extend second predetermined length $L_3$ from first set 320 of threads 324. Second set 330 of threads 334 capture epiphyseal bone in tibia 100 and/or fibula 105.

General Interpretive Principles for the Present Disclosure

Various aspects of the novel systems, apparatuses, and methods are described more fully hereinafter with reference to the accompanying drawings. The teachings disclosure may, however, be embodied in many different forms and should not be construed as limited to any specific structure or function presented throughout this disclosure. Rather, these aspects are provided so that this disclosure will be thorough and complete, and will fully convey the scope of the disclosure to those skilled in the art. Based on the teachings herein one skilled in the art should appreciate that the scope of the disclosure is intended to cover any aspect of the novel systems, apparatuses, and methods disclosed herein, whether implemented independently of or combined with any other aspect of the disclosure. For example, a system or an apparatus may be implemented, or a method may be practiced using any one or more of the aspects set forth herein. In addition, the scope of the disclosure is intended to cover such a system, apparatus or method which is practiced using other structure, functionality, or structure and functionality in addition to or other than the various aspects of the disclosure set forth herein. It should be understood that any aspect disclosed herein may be set forth in one or more elements of a claim. Although some benefits and advantages of the preferred aspects are mentioned, the scope of the disclosure is not intended to be limited to particular benefits, uses, or objectives. The detailed description and drawings are merely illustrative of the disclosure rather than limiting, the scope of the disclosure being defined by the appended claims and equivalents thereof.

With respect to the use of plural vs. singular terms herein, those having skill in the art can translate from the plural to the singular and/or from the singular to the plural as is appropriate to the context and/or application. The various singular/plural permutations may be expressly set forth herein for sake of clarity.

When describing an absolute value of a characteristic or property of a thing or act described herein, the terms "substantial," "substantially," "essentially," "approximately," and/or other terms or phrases of degree may be used without the specific recitation of a numerical range. When applied to a characteristic or property of a thing or act described herein, these terms refer to a range of the characteristic or property that is consistent with providing a desired function associated with that characteristic or property.

In those cases where a single numerical value is given for a characteristic or property, it is intended to be interpreted as at least covering deviations of that value within one significant digit of the numerical value given.

If a numerical value or range of numerical values is provided to define a characteristic or property of a thing or act described herein, whether or not the value or range is qualified with a term of degree, a specific method of measuring the characteristic or property may be defined herein as well. In the event no specific method of measuring the characteristic or property is defined herein, and there are different generally accepted methods of measurement for the characteristic or property, then the measurement method should be interpreted as the method of measurement that would most likely be adopted by one of ordinary skill in the art given the description and context of the characteristic or property. In the further event there is more than one method of measurement that is equally likely to be adopted by one of ordinary skill in the art to measure the characteristic or property, the value or range of values should be interpreted as being met regardless of which method of measurement is chosen.

It will be understood by those within the art that terms used herein, and especially in the appended claims (e.g., bodies of the appended claims) are intended as "open" terms unless specifically indicated otherwise (e.g., the term "including" should be interpreted as "including but not limited to," the term "having" should be interpreted as "having at least," the term "includes" should be interpreted as "includes but is not limited to," etc.).

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a"

or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

In those instances where a convention analogous to "at least one of A, B, and C" is used, such a construction would include systems that have A alone, B alone, C alone, A and B together without C, A and C together without B, B and C together without A, as well as A, B, and C together. It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include A without B, B without A, as well as A and B together."

Various modifications to the implementations described in this disclosure can be readily apparent to those skilled in the art, and generic principles defined herein can be applied to other implementations without departing from the spirit or scope of this disclosure. Thus, the disclosure is not intended to be limited to the implementations shown herein but is to be accorded the widest scope consistent with the claims, the principles and the novel features disclosed herein. The word "exemplary" is used exclusively herein to mean "serving as an example, instance, or illustration." Any implementation described herein as "exemplary" is not necessarily to be construed as preferred or advantageous over other implementations.

Certain features that are described in this specification in the context of separate implementations also can be implemented in combination in a single implementation. Conversely, various features that are described in the context of a single implementation also can be implemented in multiple implementations separately or in any suitable sub-combination. Moreover, although features can be described above as acting in certain combinations and even initially claimed as such, one or more features from a claimed combination can in some cases be excised from the combination, and the claimed combination can be directed to a sub-combination or variation of a sub-combination.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

The invention claimed is:

1. A threaded implant for bone fixation, comprising:
- a head; and
- a shaft extending distally from the head, the shaft comprising:
  - a threaded portion extending continuously from a distal tip of the shaft, the threaded portion comprising:
    - a first set of threads extending, from the distal tip, a first predetermined length, the first set of threads configured to capture cortical bone in one of a foot and/or ankle bone of a patient, and
    - a second set of threads extending, from the first set of threads, a second predetermined length, the second set of threads configured to capture epiphyseal bone in the one of the foot and/or ankle bone, wherein:
  - the threaded portion of the shaft has a constant diameter along the second predetermined length and along the first predetermined length except for a distal portion of the first predetermined length along which the shaft tapers to the distal tip,
  - the constant diameter is approximately 50% of a constant diameter of the second set of threads, and
  - a constant diameter of the first set of threads, except along the distal portion of the first predetermined length, is approximately 75% of the constant diameter of the second set of threads.

2. The threaded implant of claim 1, wherein the head comprises a drive feature.

3. The threaded implant of claim 1, wherein:
- the first set of threads taper along the distal portion of the first predetermined length toward the distal tip.

4. The threaded implant of claim 1, wherein a proximal portion of the shaft, from the second set of threads to the head of the implant, is not threaded.

5. The threaded implant of claim 1, wherein:
- the first predetermined length is based at least in part on a total length of the implant; and
- the second predetermined length has a static value regardless of the total length of the implant.

6. The threaded implant of claim 1, wherein a pitch of the first set of threads is equal to a pitch of the second set of threads.

7. The threaded implant of claim 1, the shaft further comprising a plurality of cutting flutes, at least one of the plurality of cutting flutes disposed immediately adjacent the distal tip and at least one of the plurality of cutting flutes disposed at a transition between the first and second sets of threads.

8. The threaded implant of claim 1, wherein:
- the implant is configured to provide maximum interfragmentary compression when inserted perpendicular to a fracture line of the one of the foot and/or ankle bone; and
- the implant is configured to provide resistance to shear forces induced by axial loading of the one of the foot and/or ankle bone when inserted perpendicular to the long axis of the one of the foot and/or ankle bone.

9. A method of fixing a bone with a threaded implant, comprising:
- disposing a distal tip of a shaft of the threaded implant adjacent to or against a surface of a foot and/or ankle bone of a patient; and
- rotationally driving a head of the threaded implant that is coupled to the shaft until a first set of threads of a threaded portion of the shaft, extending a first predetermined length from the distal tip, capture cortical bone in the foot and/or ankle bone, and a second set of threads of the threaded portion of the shaft, extending a second predetermined length from the first set of threads, capture epiphyseal bone in the foot and/or ankle bone, wherein:
- the threaded portion of the shaft has a constant diameter along the second predetermined length and along the first predetermined length except for a distal portion of the first predetermined length along which the shaft tapers to the distal tip, the constant diameter of the threaded portion of the shaft is approximately 50% of a constant diameter of the second set of threads, and a constant diameter of the first set of threads, except along the distal portion of the first predetermined length, is approximately 75% of the constant diameter of the second set of threads.

10. The method of claim 9, wherein the head comprises a drive feature.

11. The method of claim 9, wherein:

the first set of threads taper along the distal portion of the first predetermined length toward the distal tip.

12. The method of claim 9, wherein a proximal portion of the shaft, from the second set of threads to the head of the implant, is not threaded.

13. The method of claim 9, wherein:

the first predetermined length is based at least in part on a total length of the implant; and the second predetermined length has a static value regardless of the total length of the implant.

14. The method of claim 9, wherein a pitch of the first set of threads is equal to a pitch of the second set of threads.

15. The method of claim 9, the shaft further comprising a plurality of cutting flutes, at least one of the plurality of cutting flutes disposed immediately adjacent the distal tip and at least one of the plurality of cutting flutes disposed at a transition between the first and second sets of threads.

16. The method of claim 9, wherein:

the implant is configured to provide maximum interfragmentary compression when inserted perpendicular to a fracture line of the one of the foot and/or ankle bone; and the implant is configured to provide resistance to shear forces induced by axial loading of the one of the foot and/or ankle bone when inserted perpendicular to the long axis of the one of the foot and/or ankle bone.

17. A method of manufacturing a threaded implant for bone fixation, comprising:

forming a head of the threaded implant; and forming a shaft extending distally from the head and comprising:

a threaded portion extending continuously from a distal tip of the shaft, the threaded portion comprising:

a first set of threads extending, from the distal tip, a first predetermined length, the first set of threads configured to capture cortical bone in one of a foot and/or ankle bone of a patient, and a second set of threads extending, from the first set of threads, a second predetermined length, the second set of threads configured to capture epiphyseal bone in the one of the foot and/or ankle bone, wherein:

the threaded portion of the shaft has a constant diameter along the second predetermined length and along the first predetermined length except for a distal portion of the first predetermined length along which the shaft tapers to the distal tip, the constant diameter is approximately 50% of a constant diameter of the second set of threads, and a constant diameter of the first set of threads, except along the distal portion of the first predetermined length, is approximately 75% of the constant diameter of the second set of threads.

18. The method of claim 17, wherein forming the head comprises forming or otherwise providing a drive feature in the head.

19. The method of claim 17, wherein the head is formed to have a thickness and a diameter.

20. The method of claim 17, wherein:

the first set of threads taper along the distal portion of the first predetermined length toward the distal tip.

21. The method of claim 17, wherein the shaft is formed such that a proximal portion of the shaft, from the second set of threads to the head of implant, is not threaded.

22. The method of claim 17, wherein the shaft is formed such that:

the first predetermined length is based at least in part on a total length of the implant; and the second predetermined length has a static value regardless of the total length of the implant.

23. The method of claim 17, wherein the shaft is formed such that a pitch of the first set of threads is equal to a pitch of the second set of threads.

24. The method of claim 17, wherein the shaft is formed to further comprise a plurality of cutting flutes, at least one of the plurality of cutting flutes disposed immediately adjacent the distal tip and at least one of the plurality of cutting flutes disposed at a transition between the first and second sets of threads.

25. The method of claim 17, wherein:

the implant is configured to provide maximum interfragmentary compression when inserted perpendicular to a fracture line of the one of the foot and/or ankle bone; and the implant is configured to provide resistance to shear forces induced by axial loading of the one of the foot and/or ankle bone when inserted perpendicular to the long axis of the one of the foot and/or ankle bone.

* * * * *